(12) United States Patent
Yi et al.

(10) Patent No.: US 9,241,648 B2
(45) Date of Patent: Jan. 26, 2016

(54) DEVICE FOR MEASUREMENT FOR BIONIC INFORMATION

(75) Inventors: Sung Il Yi, Seoul (KR); Ki Young Kim, Bucheon (KR); Kang Eun Kim, Seoul (KR); Chang Heon Kang, Ansan (KR)

(73) Assignee: KOREA INSTITUTE OF INDUSTRIAL TECHNOLOGY, Cheonan (KR)

(*) Notice: Subject to any disclaimer, the term of this patent is extended or adjusted under 35 U.S.C. 154(b) by 103 days.

(21) Appl. No.: 13/394,905

(22) PCT Filed: Sep. 8, 2010

(86) PCT No.: PCT/KR2010/006107
§ 371 (c)(1),
(2), (4) Date: Mar. 8, 2012

(87) PCT Pub. No.: WO2011/031061
PCT Pub. Date: Mar. 17, 2011

(65) Prior Publication Data
US 2012/0172728 A1  Jul. 5, 2012

(30) Foreign Application Priority Data

Sep. 8, 2009  (KR) .................. 10-2009-0084496
Sep. 8, 2009  (KR) .................. 10-2009-0084499
Sep. 8, 2009  (KR) .................. 10-2009-0084505
Sep. 8, 2009  (KR) .................. 10-2009-00845511

(51) Int. Cl.
*A61B 5/0205* (2006.01)
*A61B 5/0402* (2006.01)
*A61B 5/024* (2006.01)
*A61B 5/053* (2006.01)
*A61B 5/00* (2006.01)

(52) U.S. Cl.
CPC ............... *A61B 5/0402* (2013.01); *A61B 5/024* (2013.01); *A61B 5/0537* (2013.01); *A61B 5/4872* (2013.01); *A61B 5/6824* (2013.01)

(58) Field of Classification Search
CPC .... A61B 5/024; A61B 5/0537; A61B 5/4872; A61B 5/0402; A61B 5/6824
USPC .................................. 600/322, 473, 474, 483
See application file for complete search history.

(56) References Cited

U.S. PATENT DOCUMENTS 5,615,672 A * 4/1997 Braig et al. .................. 600/474
5,875,257 A * 2/1999 Marrin et al. ................ 382/107
6,064,753 A * 5/2000 Bolle et al. ................... 382/125
(Continued)

FOREIGN PATENT DOCUMENTS

JP  06-125881 A  5/1994
JP  11033007 A  2/1999
(Continued)

*Primary Examiner* — Baisakhi Roy
(74) *Attorney, Agent, or Firm* — Patent Office of Dr. Chung Park (57) ABSTRACT

There is disclosed an apparatus for measuring biometric information that can perform precise and comprehensive measurement by measuring biometric information about an examinee taking a more comfortable position. The apparatus for measuring biometric information includes a hand rest comprising a hand rest part formed in a concave curvature shape to have an examinee's hand put thereon, to contact with an examinee's palm and fingers; and a measurement part provided in the hand rest part to measure the examinee's biometric information.

11 Claims, 8 Drawing Sheets

(56) References Cited

U.S. PATENT DOCUMENTS

| | | | |
|---|---|---|---|
| RE40,116 E * | 2/2008 | Engstrom | 455/66.1 |
| 2001/0000526 A1 * | 4/2001 | Gopinathan | A61B 5/0002 |
| | | | 600/300 |
| 2001/0034491 A1 | 10/2001 | Benson et al. | |
| 2001/0056227 A1 | 12/2001 | Gopinathan et al. | |
| 2002/0045805 A1 * | 4/2002 | Gopinathan et al. | 600/300 |
| 2002/0150282 A1 * | 10/2002 | Kinsella | 382/124 |
| 2004/0128519 A1 * | 7/2004 | Klinger et al. | 713/186 |
| 2004/0246231 A1 * | 12/2004 | Large | 345/163 |
| 2006/0020216 A1 * | 1/2006 | Oishi et al. | 600/500 |
| 2007/0055888 A1 * | 3/2007 | Miller et al. | 713/186 |
| 2008/0208018 A1 * | 8/2008 | Ridder et al. | 600/322 |
| 2008/0223926 A1 * | 9/2008 | Miller et al. | 235/382 |
| 2009/0287100 A1 * | 11/2009 | Aranciva | 600/500 |
| 2009/0306487 A1 * | 12/2009 | Crowe et al. | 600/322 |
| 2010/0248822 A1 * | 9/2010 | Migos et al. | 463/29 |
| 2010/0327002 A1 * | 12/2010 | Hegan et al. | 221/30 |
| 2012/0172729 A1 * | 7/2012 | Yi et al. | 600/483 |

FOREIGN PATENT DOCUMENTS

| | | |
|---|---|---|
| JP | 2000217794 A | 8/2000 |
| JP | 2001-187029 A | 7/2001 |
| JP | 2005087483 A | 4/2005 |
| JP | 2008061831 A | 3/2008 |
| KR | 200226025 Y1 | 6/2001 |
| KR | 10-2001-0093524 A | 10/2001 |
| KR | 1020090044238 A | 5/2009 |

* cited by examiner

DEVICE FOR MEASUREMENT FOR BIONIC INFORMATION

CROSS-REFERENCE TO PRIOR APPLICATIONS

This application is a national Stage Patent Application of PCT International Patent Application No. PCT/KR2010/006107, filed on Sep. 8, 2010 under 35 U.S.C. §371, which claims priority of Korean Patent Application Nos. 10-2009-0084496, filed on Sep. 8, 2009, 10-2009-0084499 filed on Sep. 8, 2009, 10-2009-0084505 filed on Sep. 8, 2009, and 10-2009-0084511 filed on Sep. 8, 2009 which are all hereby incorporated by reference in their entirety.

TECHNICAL FIELD

Embodiments of the invention may relate to an apparatus for measuring biometric information, more particularly to, an apparatus for measuring biometric information that can perform precise and comprehensive measurement by measuring biometric information about an examinee taking a more comfortable position.

BACKGROUND

Recently, there have been increasing concerns and demands for medical check-up, as the living standard and health-consciousness are improving. In a typical medical check-up, a blood pressure, a pulse wave, an electrocardiogram (EKG) and body fat are measured and utilized as basic data.

For that, each of medical offices is equipped with a sphygmomanometer for measuring the blood pressure, an electrocardiograph for measuring the electrocardiogram, a body fat meter for measuring the body fat, a pressurized pulse waveform for measuring the pulse wave and a plethysmograpy for measuring the blood flow rate.

However, conventional measuring devices have following disadvantages.

First of all, a single apparatus measures one piece of biometric information and different measuring devices have to be provided to measure a variety of human information. This requires too much unnecessary space and it is difficult to repair and maintain the apparatuses. Also, an examinee has to move from one device to another device to have the measurement and he or she has inconvenience.

Moreover, a single device measures a single type of biometric information. Accordingly, the measured biometric information fails to be collected and it has to be inputted and utilized by a human resource. When collecting the biometric information, an error or a mistake might be generated disadvantageously.

DISCLOSURE

Technical Problem

To solve the problems, an object of the invention is to provide an apparatus for measuring biometric information that can measure a variety of biometric information as single device.

Technical Solution

To achieve these objects and other advantages and in accordance with the purpose of the embodiments, as embodied and broadly described herein, an apparatus for measuring biometric information includes a hand rest comprising a hand rest part formed in a concave curvature shape to have an examinee's hand put thereon, to contact with an examinee's palm and fingers; and a measurement part provided in the hand rest part to measure the examinee's biometric information.

A finger seating recess formed may be a corresponding shape to each of human fingers is provided in the hand rest to seat the examinee's finger thereon.

The biometric information measured by the measurement part may be at least one of an electrocardiogram, body fat and a plethysmogram.

The measurement part may be a plethysmogram sensor provided in a predetermined position of the finger seating recess to contact with the examinee's fingers, to measure blood flow variation of the examinee's fingers, the plethysmogram sensor comprising an infrared ray emitting part and an infrared ray receiving part.

The measurement part may be an electrocardiogram measuring unit configured to measure the examinee's electrocardiogram.

Two hand rests may be provided corresponding to the examinees' right and left hands, respectively, and the electrocardiogram measuring unit may include a first electrocardiogram sensor and a second electrocardiogram sensor provided in palm and finger contactable portions of one of the two hand rests corresponding to the examinee's left and right hands, respectively; and a third electrocardiogram sensor provided in a palm or finger contactable portion of the other one of the two hand rests corresponding to the examinee's left and right hands, and the electrocardiogram measuring unit may sense electric activity generated in the examinee's heartbeat.

The measurement part may be a body fat measuring unit configured to measure the examinee's body fat.

Two hand rests may be provided corresponding to the examinee's right and left hands, respectively, and the body fat measuring unit may include a first body fat sensor and a second body fat sensor provided in finger contactable portions of one of the two hand rests corresponding to the examinee's right and left hands, each of the first body fat sensor and the second body fat sensor that is able to contact with a different finger; and a third body fat sensor and a fourth body fat sensor provided in finger contactable portions of the other one of the two hand rests, each of the third and fourth body fat sensors that is able to contact with a different finger, and the body fat measuring sensor may measure the examinee's body fat.

Advantageous Effects

The embodiments have following advantageous effects.

First, the side of the housing is open and the forearm introducing part is formed. Accordingly, compared with a conventional cuff type blood pressure meter, the apparatus according to the embodiment of the invention has an advantageous effect of convenience.

Second, the forearm seating part provided in the housing to seat the forearm thereon is formed in a corresponding shape to the examinee's forearm. Accordingly, the examinee can have the measuring process in a more comfortable and precise position. The examinee's convenience as well as reliability of the measured values may be improved effectively.

Third, the hand rest is formed to seat the hand of the forearm seated in the forearm seating part. Accordingly, the examinee can have the measurement in more comfortable and precise position. The examinee's convenience as well as reliability of the measured values may be improved effectively.

Fourth, the hand rest can be sliding along the longitudinal direction of the forearm, to be adjustable for an optimized position even to the examinee having a shorter forearm or a long forearm. Accordingly, the examinee's convenience as well as reliability of the measured values may be improved effectively.

Fifth, the various types of the measuring units are provided and various types of biometric information can be achieved. Without various measurement equipments, the cost for equipping the measurement equipments can be reduced and convenience in repair and maintenance may be enhanced. Also, plural measuring devices need not be provided and less space is required. Moreover, a variety of biometric information can be acquired at one time and convenience of the examination can be enhanced. The acquired information is automatically collected and mistakes that might be generated by errors can be reduced. Different types of biometric information can be fused smoothly.

Sixth, when measuring the pressurized pulse waveform, the upper armlet presses the upper side of the wrist area in the forearm uniformly. Accordingly, the pressurized pulse waveform positioned under the pressed wrist area can be in contact with the wrist area by the fixed force. The reliability of the measured values can be improved effectively.

BRIEF DESCRIPTION OF THE DRAWINGS

Arrangements and embodiments may be described in detail with reference to the following drawings in which like reference numerals refer to like elements and wherein.

BEST MODE

As follows, embodiments will be described in detail to be embodied by those skilled in the art to which the embodiments pertain to, in reference to the accompanying drawings. Reference may now be made in detail to specific embodiments, examples of which may be illustrated in the accompanying drawings. Wherever possible, same reference numbers may be used throughout the drawings to refer to the same or like parts.

Figure 1:
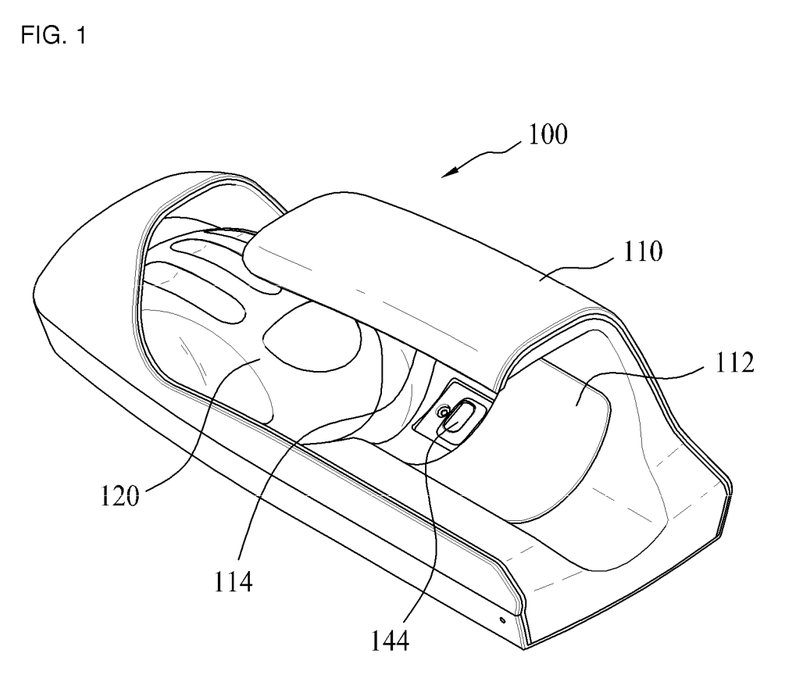
FIG. 1 is a perspective view illustrating an apparatus for measuring biometric information according to an embodiment of the invention.
Figure 2:
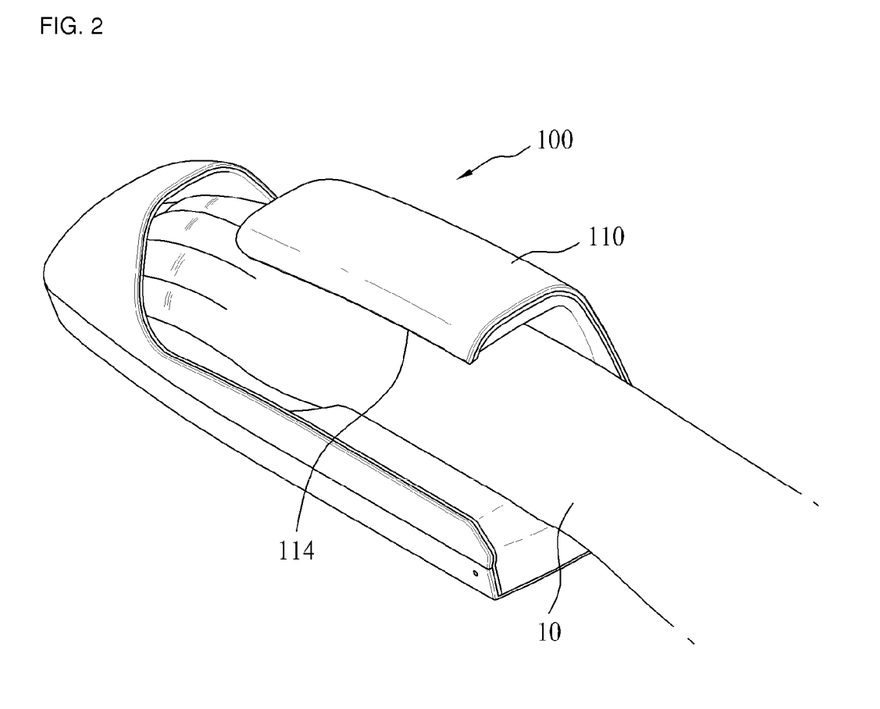
FIG. 2 is a perspective view illustrating the apparatus shown in FIG. 1 that has an examiner's forearm seated thereon.

As shown in FIGS. 1 and 2, an apparatus for measuring biometric information (hereinafter, a biometric measuring apparatus) according to this embodiment includes a housing 110, a hand rest 120 and a measuring part.

Meanwhile, a shoulder part of a human body between the elbow and the shoulder is called as 'the upper arm' and a part of a human body between the elbow and the wrist is called as 'the forearm'

The housing 110 defines an exterior appearance of the biometric information measuring apparatus and it forms a forearm seating part 112. The forearm seating part 112 may be formed in an arc shape corresponding to a human forearm. Also, the housing 110 may have an approximately C-shaped appearance with an open side, to form a forearm introducing part 114 having an open portion to allow the examinee's forearm to be introduced into the forearm seating part 112 smoothly.

The hand rest 120 is provided in front of the forearm seating part 112 of the housing 110. The hand rest 120 is a component where the hand of the forearm seated on the forearm seating part 112 is seated and it is formed in a concave curvature shape similar to a mouse for a computer.

Figure 3:
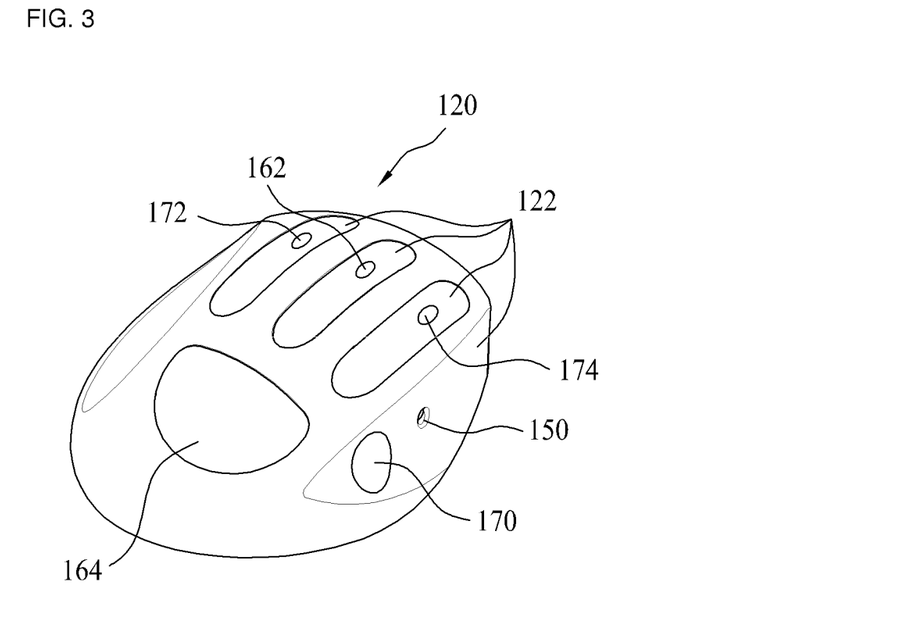
FIG. 3 is a perspective view illustrating a hand rest shown in FIG. 1.

Also, a finger seating recess 112 may be formed in a surface of the hand rest 120 to seat each finger of the hand put on the hand rest 120, in a corresponding shape to a human finger.

Figure 4:
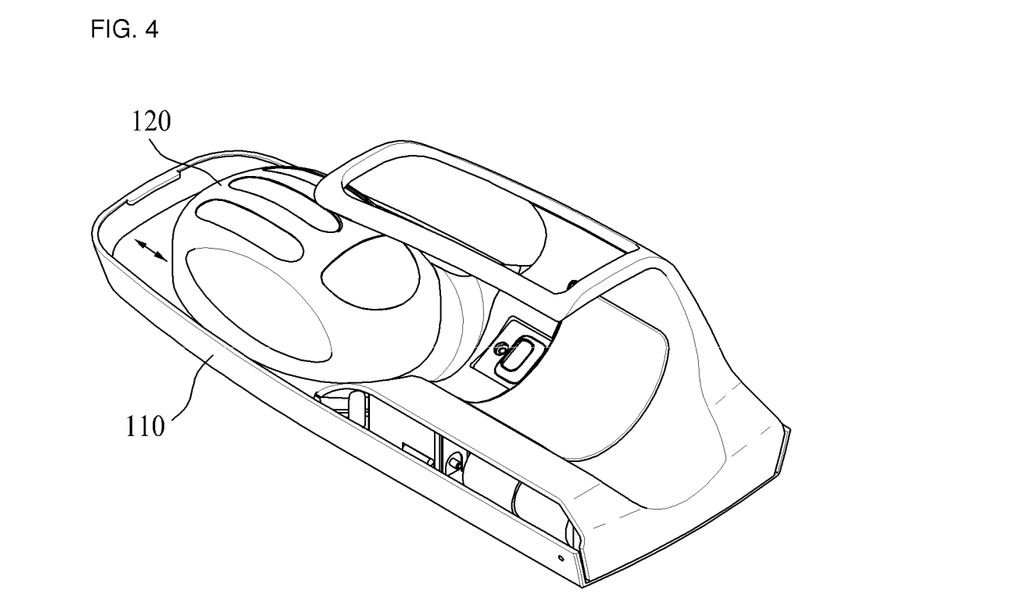
FIG. 4 is a perspective view illustrating the hand rest of FIG. 3 that is sliding with respect to a housing.

Meanwhile, considering that everybody has a different length of the forearm, the hand rest 120 may be sliding forwardly and backwardly along a longitudinal direction of the forearm with respect to the housing 110, as shown in FIG. 4. Accordingly, the hand rest 120 can have an optimized position that can be adjustable for a person having a short forearm or a long forearm.

Meanwhile, the measurement part is a component configured to measure the examinee's biometric information and it is provided in the housing 110 or the hand rest 120. The measurement part may be at least one of a blood pressure measuring unit, a pressurized pulse waveform measuring unit, a plethysmogram measuring unit, an electrocardiogram measuring unit a body fat measuring unit.

In this instance, the expression of "at least one of" means one or more than two.

Of course, another type of a measuring unit may be provided, rather than those measuring units.

Figure 5:
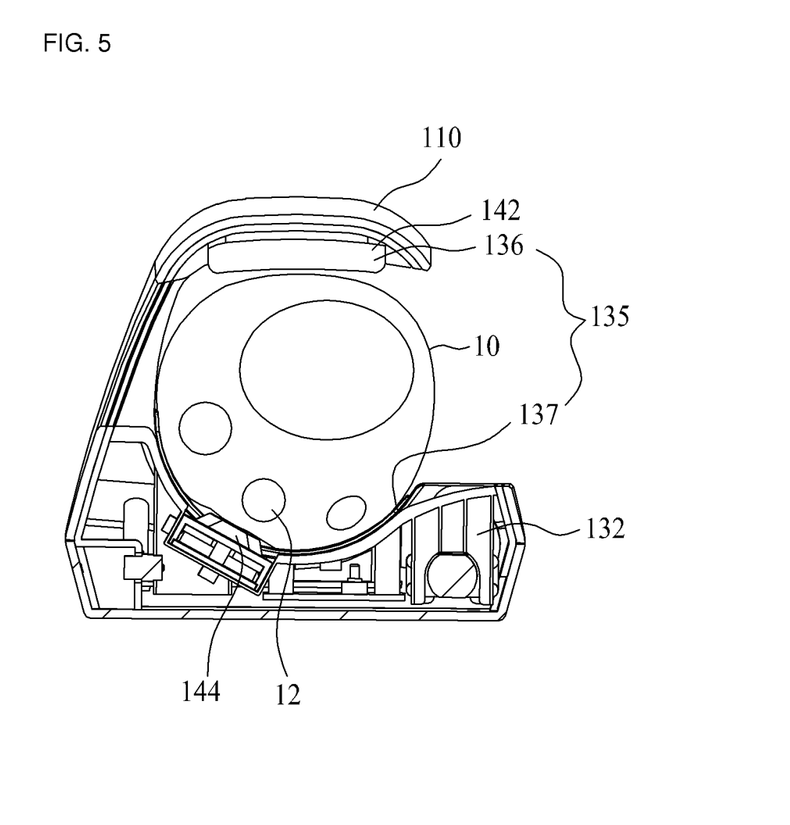
FIG. 5 is a sectional view of FIG. 2.
Figure 6:
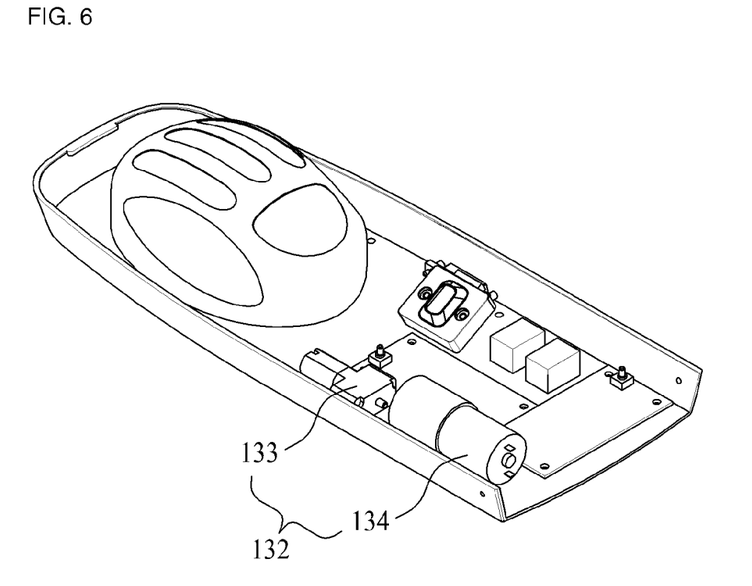
FIG. 6 is an exploded perspective view illustrating a pneumatic driving part of the apparatus for measuring the biometric information shown in FIG. 1.

The blood pressure measuring unit is configured to measure a blood pressure by pressing the examinee's forearm seated on the forearm seating part. As shown in FIGS. 5 and 6, the blood pressure measuring unit may include a pneumatic driving part 132, a pneumatic armlet 135, a valve (not shown) and a blood pressure measuring sensor (not shown).

The pneumatic driving part 132 is configured to generate a pneumatic pressure.

Also, the pneumatic armlet 135 is provided in the forearm seating part, as shown in FIG. 5, and it is connected with the pneumatic driving part 132 to pressure the examinee's forearm by using the pneumatic pressure generated in the pneumatic driving part 132. The valve (not shown) selectively exhausts the air applied to the pneumatic armlet 135 and the blood pressure measuring sensor (not shown) measures the blood pressure based on pneumatic pressure variation of the pneumatic armlet 135 pressing the forearm. The valve (not shown) and the blood pressure measuring sensor (not shown) may be provided in an air passage (not shown) connecting the pneumatic driving part 132 and the pneumatic armlet 135 with each other and pneumatic armlet 132 or the pneumatic driving part 132.

Also, as shown in FIG. 5, the pneumatic armlet 135 may be divided into an upper armlet 136 and a lower armlet 137.

The upper armlet 136 is positioned in an inner upper surface of the forearm seating part 112 composing the housing 110 and it press an upper side of the examinee's forearm. In this instance, the upper armlet 136 may be configured to press the wrist area and its neighboring area of the forearm.

Also, the lower armlet 137 is positioned in an inner lower surface of the forearm seating part 112 composing the housing 110 and it presses a lower side of the examinee's forearm.

When the pneumatic armlet 135 is divided into the upper armlet 136 and the lower armlet 137, the pneumatic driving part 132 may be configured of a first pneumatic pump 133 and a second pneumatic pump 134. The first pneumatic pump 133 may supply air to the upper armlet 136 and the second pneumatic pump 134 may supply air to the lower armlet 137.

The pressurized pulse waveform measuring unit is a component configured to figure out a minute-based heart rate and a vascular compliance based on a pulse waveform of a vessel 12 measured by a pressure sensor, while applying a pressure to a vessel 12 in the forearm's wrist area.

Typically, when measuring the pulse wave, it is important to apply a precise pressure to a precise position of a vessel in the wrist area.

As a result, the pressurized pulse waveform measuring unit includes an upper press cuff 142 and a pressurized pulse waveform sensor 144 as shown in FIG. 5.

The upper press cuff 142 is provided in an inner surface of the housing, above the forearm seating part 112, to press an upper side of the examinee's wrist area.

The upper press cuff 142 may be the same component as the upper armlet 136 of the blood measuring unit mentioned above or it may be a separated component from the upper armlet 136 of the blood pressure measuring unit. If the upper press cuff 142 is a separated component from the upper armlet 136 of the blood pressure unit, an auxiliary driving part such as an air pump (not shown) may be provided to drive the upper press cuff 142.

The pressurized pulse waveform sensor 144 is a kind of a pressure sensor and it is provided in close contact with the lower side of the wrist area pressed by the upper press cuff 142 to pressure variation of the vessel 12 of the wrist area.

Figure 7:
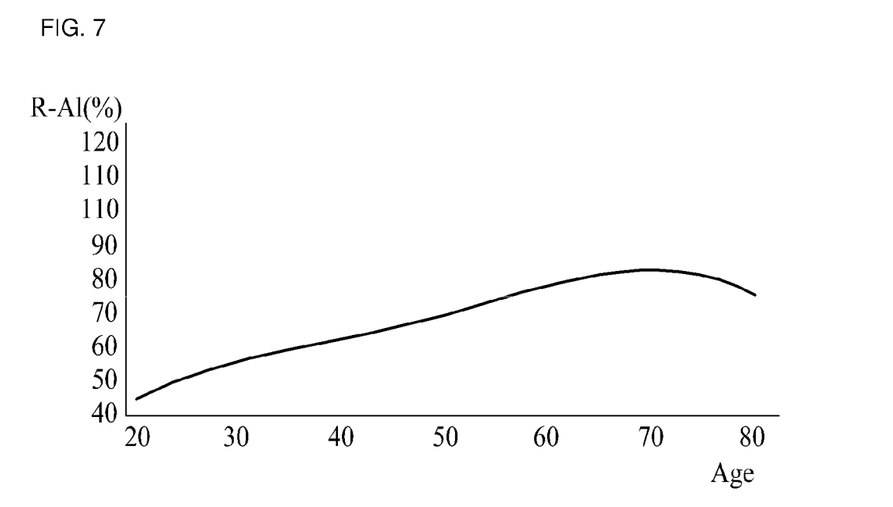
FIG. 7 is a diagram illustrating a graph of a vessel compliance gained by a pulse wave measuring device shown in FIG. 1.

The upper press cuff 142 presses the wrist area toward the pressurized pulse waveform sensor 144 with a predetermined pressure. Accordingly, information on the minute-based heartbeat and the vascular compliance (R-AI) based on the pressure applied by the upper armlet 136 and the pressure measured by the pressurized pulse wave form sensor 144, as shown in FIG. 7.

The plethysmogram measuring unit is a component configured to measure a blood flow rate of the blood flowing to a top of a finger and a pulse waveform.

The plethysmogram measuring unit is a photo sensor that measures a blood flow rate of the blood flowing to a peripheral portion and a pulse waveform and it includes a plethysmogram sensor 150. The plethysmogram sensor 150 includes an infrared ray emitting part and an infrared ray receiving part that are provided in the finger seating recess 122 where the finger seated on the hand rest 120 is positioned to measure the blood flow rate of the blood flowing to the peripheral portion and the pulse waveform.

Preferably, as shown in FIG. 3, the plethysmogram sensor 150 may be provided in the finger seating groove 122 where a thumb is seated.

Figure 8:
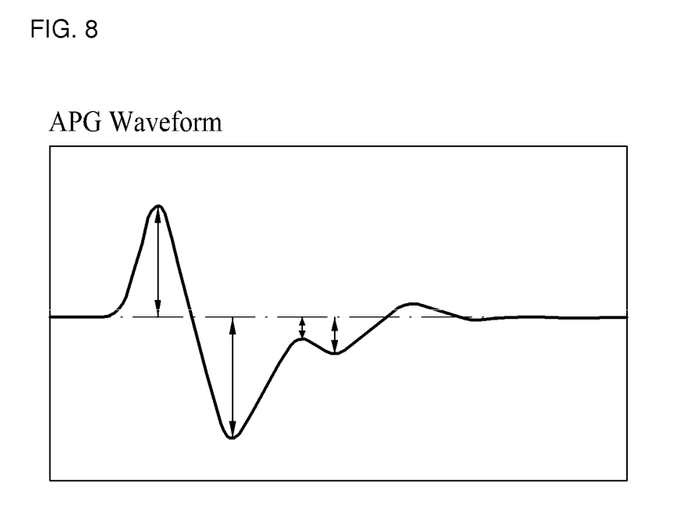
FIG. 8 is a diagram illustrating a graph of accelerated plethysmogram gained by a plethysmogram measuring device shown in FIG. 1.

The information gained by the plethysmogram measuring unit may include the minute-based heartbeat, the heart rate variable (HRV) and accelerated plethysmogram (APG) as shown in FIG. 8. Also, a cardiovascular disease such as a vaso-aging degree and blood circulatory disturbance may be diagnosed in good time based on a pattern of the accelerated plethysmogram measured by the plethysmogram sensor 150.

Figure 9:
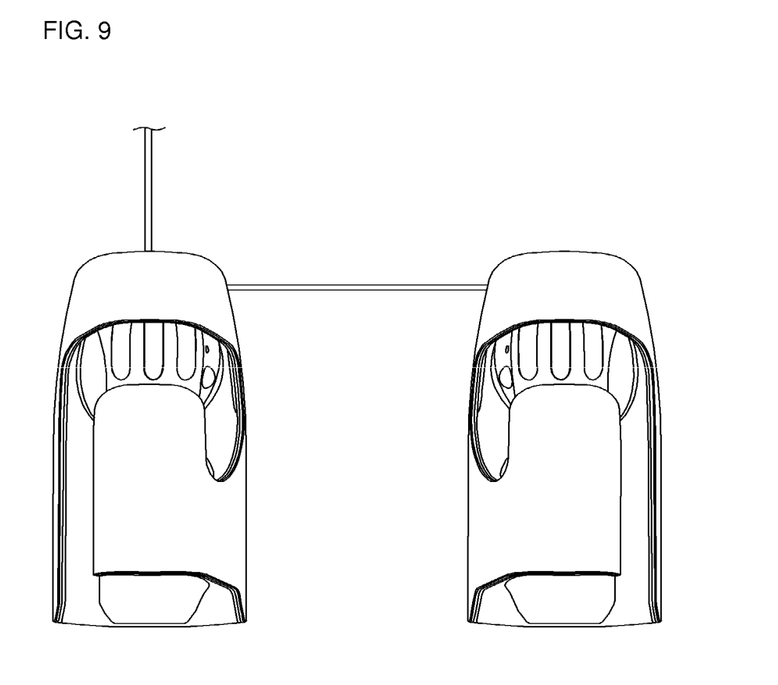
FIG. 9 is a plane view illustrating two apparatuses for measuring biometric information for right and left hands.

Meanwhile, when the measurement part includes an electrocardiogram measuring unit, the biometric information measuring apparatus 100 may include two pairs of housings and hand rests corresponding to the right and left hands, as shown in FIG. 9.

"Electrocardiography (EGG)" means a record of electric activity generated in the heart whenever the heart beats. After electrons are attached to a predetermined area of an examinee's skin, electrons are combined variously and electrocardiogram signals are recorded in a storage device.

According to this embodiment, augmented lead that measures and records heart activity in three directions may be used to amplify a minute human voltage gained from an electron. The augmented lead is a unipolar lead. Out of three leads, one lead has a positive polarity and the other two leads have a negative polarity. Displacement of the heart in a positive-polarized augmented area is amplified and utilized.

Generally, when using three electrons, electrons are attached to both hands and a foot. In this embodiment, electrons are in contact with the fingers and the palm of both hands, to improve measuring efficiency.

Electrons of the electrocardiogram may be provided in the hand rest 120. More specifically, a first electrocardiogram sensor 162 and a second electrocardiogram sensor 164 may be provided in palm and finger contactable portions in one of the hand rests 120 corresponding to the right and left hands. A third electrocardiogram sensor (not shown) may be provided in a palm or finger contactable portion in the other one of the hand rests 120 corresponding to the right and left hands.

Figure 10:
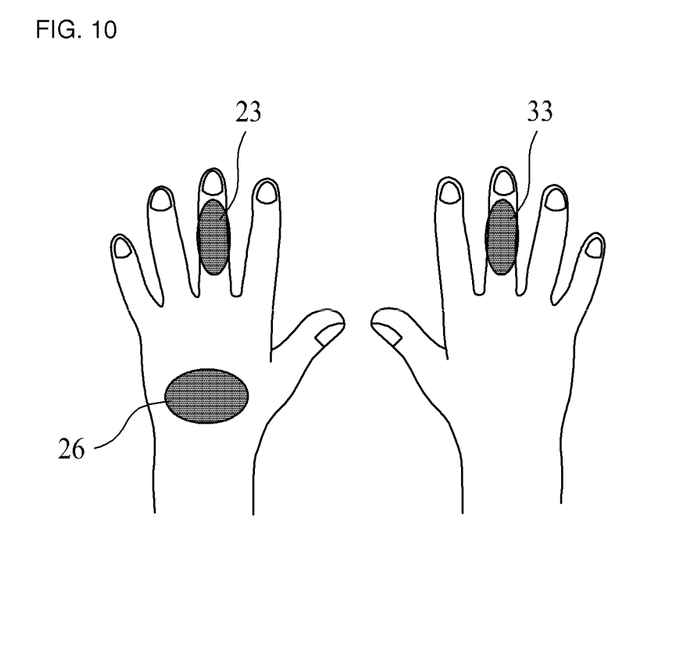
FIG. 10 is a plane view illustrating an area of a hand contacting with a electrocardiogram measuring device of the apparatus for measuring the biometric information shown in FIG. 1.

According to this embodiment, as shown in FIG. 10, the first electrocardiogram sensor 162 may contact with a middle finger of the left hand and the second electrocardiogram sensor 164 may contact with a palm 26 of the left hand. The third electrocardiogram sensor (not shown) may contact a middle finger 33 of the right hand.

As a result, the first electrocardiogram sensor 162 may be provided in a finger seating recess 122 corresponding to a middle finger of the hand rest 120 for the left hand. The second electrocardiogram sensor 164 may be provided in a portion corresponding to a palm of the hand rest 120 for the left hand. Also, the third electrocardiogram sensor (not shown) may be provided in a finger seating recess corresponding to a middle finger of the hand rest for the right hand. The structure of the hand rests for the right and left hand are in symmetry and detailed description for the hand rests for the right and left hands will be omitted. Anyone skilled in the art may expect the structure without any problems The electrocardiogram measuring unit having the above structure is able to measure a minute-based heartbeat in real time and a hear rate variable (HRV) during a predetermined time period can be measured based on the measured minute-based heartbeats. This is related to activities of the sympathetic nervous system and the parasympathetic nervous system. A stress degree may be estimated based on the measured HRV.

Meanwhile, when the measurement part includes the body fat measuring unit, the biometric information measuring apparatus 100 may include two pairs of housing and hand rests corresponding to the right and left arms, like the measurement part including the electrocardiogram measuring unit shown in FIG. 9.

Figure 11:
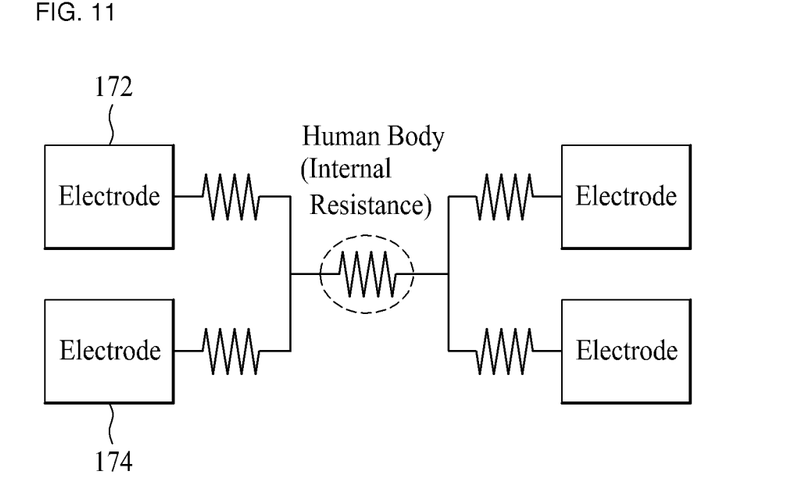
FIG. 11 is a diagram schematically illustrating a principle of measuring a body fat used by the apparatus for measuring the biometric information shown in FIG. 1.

As shown in FIG. 11, body fat measurement may be measured by analyzing resistance variation generated in the human body when currents are flowing to both electrons in contact with fingers of both hands in a bridge concept.

Figure 12:
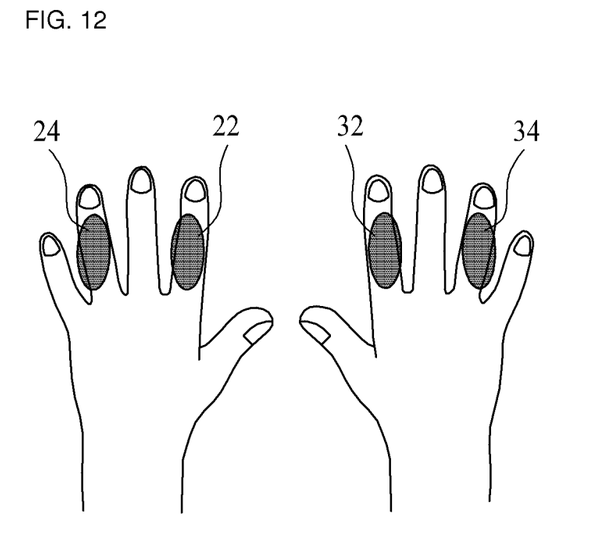
FIG. 12 is a plane view illustrating an area of a hand contacting with a body fat measuring device of the apparatus for measuring the biometric information shown in FIG. 1.
Figure 13:
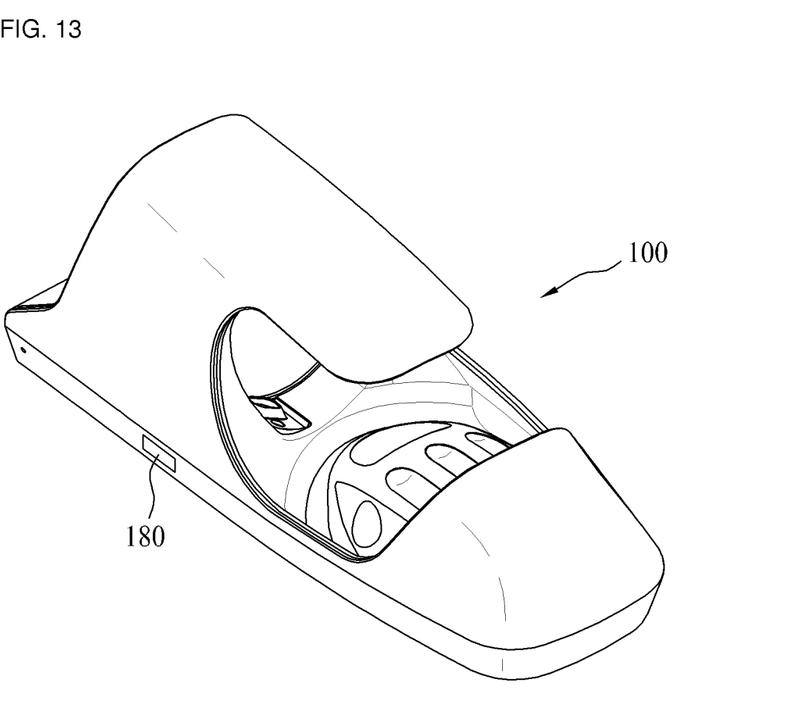
FIG. 13 is a perspective view illustrating the apparatus for measuring the biometric information shown in FIG. 1, see at a different angle.

The electrons of the body fat measuring unit may be provided in the hand rests 120. More specifically, as shown in FIG. 12, the electrons may contact with index fingers 22 and 23 and ring fingers 24 and 34 of the right and left hands. Accordingly, the electrons of the body fat measuring unit may be formed in the finger seating recesses 122 corresponding to the index and ring fingers of the right hand rest (not shown) and the left hand rest 120.

Meanwhile, the biometric information measuring apparatus may further include a release button 170 that can be used if an operational error is generated while the measurement part is measuring the biometric information or if the measuring has to be stopped because of the examinee's urgent business.

As shown in FIG. 3, the release button 170 may be provided in the finger seating recess 122 corresponding to a thumb in the hand rest 120. Accordingly, the user may push the release button 170 to stop the operation of the various sensors provided in the measurement part and the operation of the pneumatic driving part 132 and to stop the measurement.

Meanwhile, the biometric information measuring apparatus 100 according to this embodiment may further include a transmitting port 180. The transmitting port 180 is a component configured to transmit the data measured by the measurement part to and an external device such as an external analyzer, a monitor or a storage device. Of course, the transmitting port 180 may be linked via a cable or wirelessly to synchronize the biometric information measuring apparatus for the left hand and the biometric information measuring apparatus for the right hand with each other.

Meanwhile, the data gained by the plurality of the measuring units may be fused with each other, to generate new information. For example, a systolic and diastolic blood pressure value may be measured from a relation between a characteristic parameter of electrocardiographic signals and plethysmographic signals with the blood pressure.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An apparatus for measuring biometric information comprising:
   a hand rest comprising a hand rest part including a casing, a top surface of the casing having a convex curvature where the top surface of the casing including a finger recess configured to seat an examinee's finger thereon, the at least one sensor being disposed on the finger seating recess;
   a measurement part provided in the hand rest part and having a first sensor disposed to contact and read information from the examinee's palm and second, third and fourth sensors disposed to contact and read information from the middle, index and ring fingers during a measurement; and
   a release button disposed in the finger seating recess corresponding to a thumb and adapted to allow the examinee to abort a biometric measurement in progress,
   wherein the first sensor, second, third, fourth sensors, and release button are disposed to simultaneously contact the palm, middle, index, ring fingers and the thumb, respectively during the measurement.

2. The apparatus for measuring the biometric information according to claim 1, wherein a finger seating recess formed in a corresponding shape to each of human fingers is provided in the hand rest to seat the examinee's finger thereon.

3. The apparatus for measuring the biometric information according to claim 1, wherein the biometric information measured by the measurement part includes at least one of an electrocardiogram, body fat and a plethysmogram.

4. The apparatus for measuring the biometric information according to claim 3, wherein the measurement part includes a plethysmogram sensor provided in a predetermined position of the finger seating recess to contact with the examinee's fingers, to measure blood flow variation of the examinee's fingers, the plethysmogram sensor comprising an infrared ray emitting part and an infrared ray receiving part.

5. The apparatus for measuring the biometric information according to claim 3, wherein the measurement part includes an electrocardiogram measuring unit configured to measure the examinee's electrocardiogram.

6. The apparatus for measuring the biometric information according to claim 5, wherein two hand rests are provided corresponding to the examinees' right and left hands, respectively, and
   the electrocardiogram measuring unit comprises,
   a first electrocardiogram sensor and a second electrocardiogram sensor provided in palm and finger contactable portions of one of the two hand rests corresponding to the examinee's left and right hands, respectively; and
   a third electrocardiogram sensor provided in a palm or finger contactable portion of the other one of the two hand rests corresponding to the examinee's left and right hands, and
   the electrocardiogram measuring unit is adapted to sense electric activity generated in the examinee's heartbeat.

7. The apparatus for measuring the biometric information according to claim 3, wherein the measurement part includes a body fat measuring unit configured to measure the examinee's body fat.

8. The apparatus for measuring the biometric information according to claim 7, wherein two hand rests are provided corresponding to the examinee's right and left hands, respectively, and
   the body fat measuring unit comprises,
   a first body fat sensor and a second body fat sensor provided in finger contactable portions of one of the two hand rests corresponding to the examinee's right and left hands, each of the first body fat sensor and the second body fat sensor that is able to contact with a different finger; and
   a third body fat sensor and a fourth body fat sensor provided in finger contactable portions of the other one of the two hand rests, each of the third and fourth body fat sensors that is able to contact with a different finger, and
   the body fat measuring sensor is adapted to measure the examinee's body fat.

9. The apparatus for measuring the biometric information according to claim 1, further comprising:
 an upper armlet for pressing an upper side of a wrist area in the examinee's forearm during a measurement; and
 a first pneumatic pump for supplying air to the upper armlet.

10. The apparatus for measuring the biometric information according to claim 1, further comprising:
 a lower armlet for pressing a lower side of the examinee's forearm during a measurement; and
 a second pneumatic pump for supplying air to the lower armlet.

11. The apparatus for measuring the biometric information according to claim 1, further comprising:
 a transmitting port for transmitting data measure by the measurement part to an external device.

* * * * *